(12) United States Patent
Helsing et al.

(10) Patent No.: US 7,446,226 B2
(45) Date of Patent: Nov. 4, 2008

(54) CAPSAICIN DERIVATES AND THE PRODUCTION AND USE THEREOF

(75) Inventors: Torsten Helsing, Bergen (NO); Einar Bakstad, Sandnes (NO)

(73) Assignee: aXimed AS, Bergen (NO)

( * ) Notice: Subject to any disclaimer, the term of this patent is extended or adjusted under 35 U.S.C. 154(b) by 3 days.

(21) Appl. No.: 10/571,658

(22) PCT Filed: Sep. 10, 2004

(86) PCT No.: PCT/NO2004/000270

§ 371 (c)(1),
(2), (4) Date: Dec. 11, 2006

(87) PCT Pub. No.: WO2005/025314

PCT Pub. Date: Mar. 24, 2005

(65) Prior Publication Data

US 2007/0167524 A1 Jul. 19, 2007

(30) Foreign Application Priority Data

Sep. 12, 2003 (NO) .................... 20034069

(51) Int. Cl.
| | |
|---|---|
| *C07C 211/00* | (2006.01) |
| *C07C 321/00* | (2006.01) |
| *C07C 323/00* | (2006.01) |
| *C07C 381/00* | (2006.01) |
| *C07C 215/00* | (2006.01) |

(52) U.S. Cl. ............... 564/305; 564/440; 564/442; 564/443

(58) Field of Classification Search ............... 564/305, 564/440, 442, 443
See application file for complete search history.

(56) References Cited

U.S. PATENT DOCUMENTS

| 5,397,385 A | 3/1995 | Watts |
|---|---|---|
| 5,629,045 A | 5/1997 | Veech |

FOREIGN PATENT DOCUMENTS

| JP | 4208207 | 7/1992 |
|---|---|---|
| JP | 6009308 | 1/1994 |
| JP | 6080850 | 3/1994 |
| JP | 9100202 | 4/1997 |

OTHER PUBLICATIONS

Kaga, H., Miura, M., Orito, K., "A Facile Procedure for Synthesis of Capsaicin", J. Org. Chem., 1989, 54, 3477-3478.*
International Search Report for International Application No. PCT/NO2004/000270 dated Feb. 22, 2005.

* cited by examiner

*Primary Examiner*—Yvonne Eyler
*Assistant Examiner*—Jennifer Y Cho
(74) *Attorney, Agent, or Firm*—Patterson & Sheridan, L.L.P.

(57) ABSTRACT

The invention relates to new compounds, namely capsaicin derivates, a new method for their production, and their use as micro-organism-repellent agents in paints and coatings, in particular for marine installations and ships, but also for land-based structures.

11 Claims, 6 Drawing Sheets

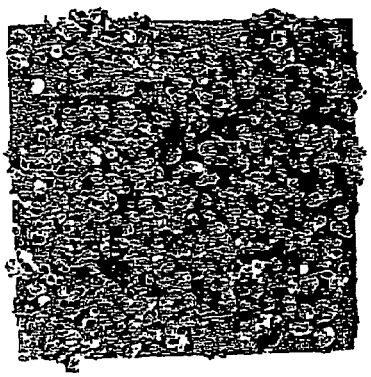
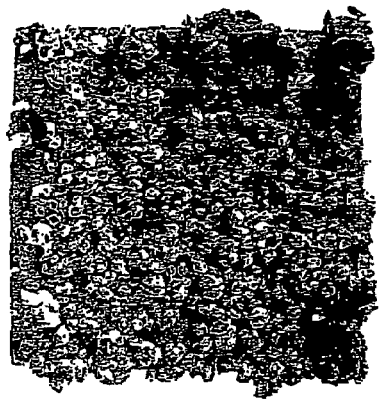
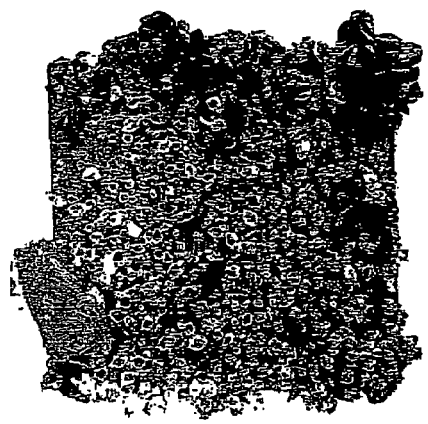
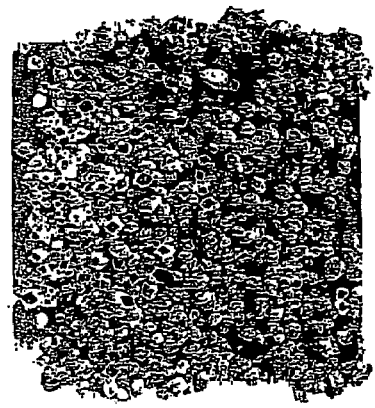
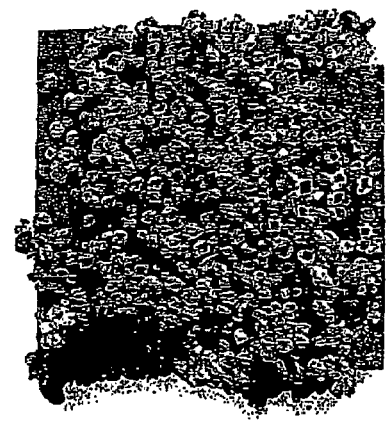
Fig. 4

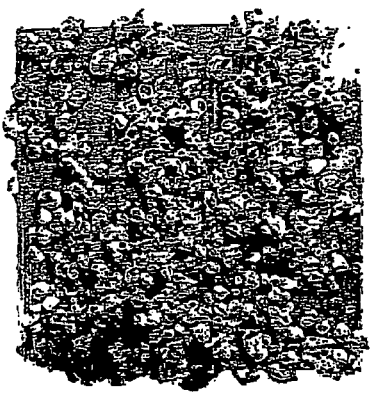
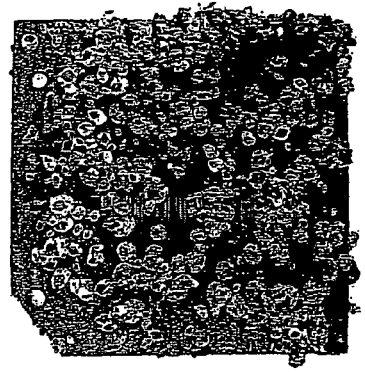
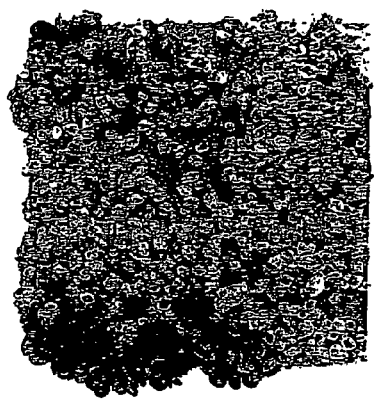
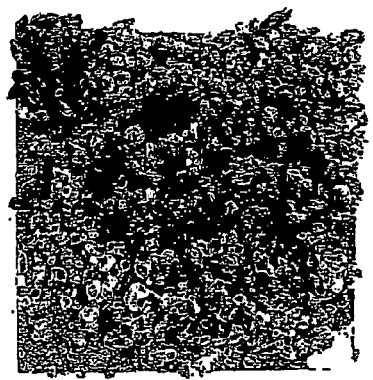
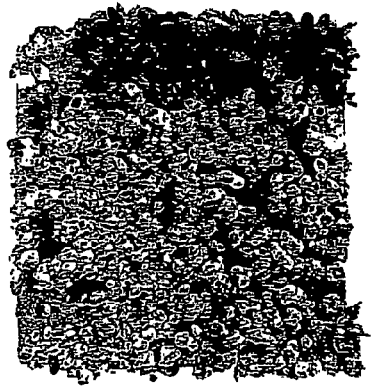
Fig. 5

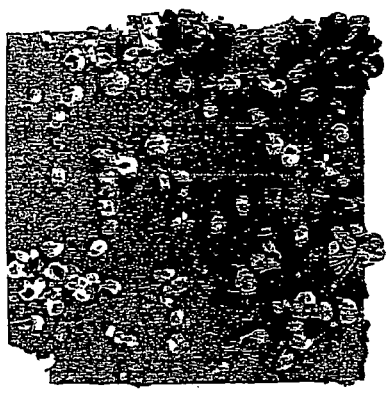
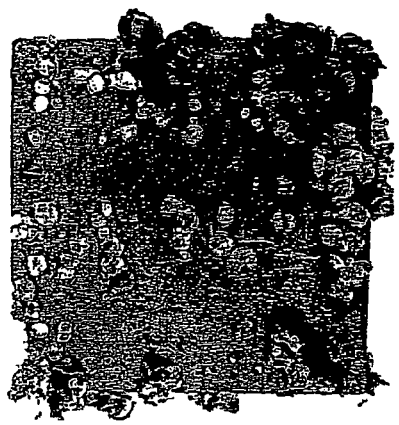
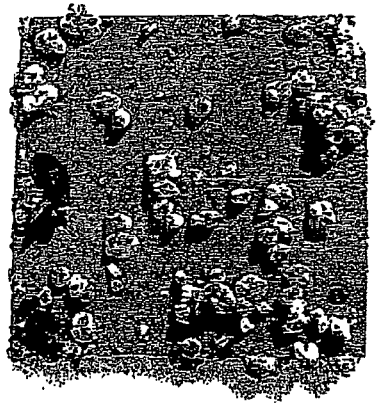
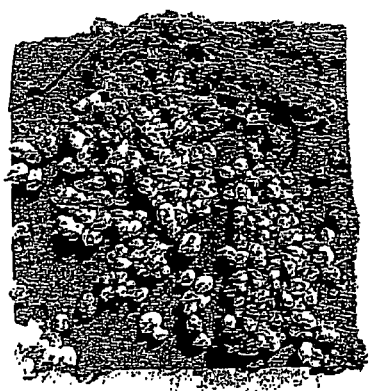
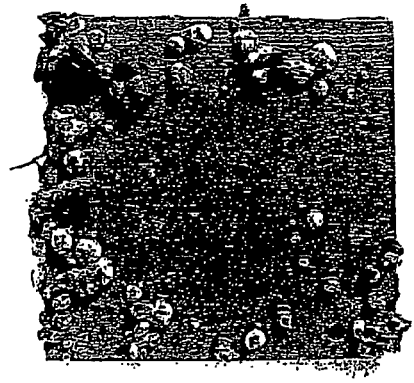
Fig. 6

CAPSAICIN DERIVATES AND THE PRODUCTION AND USE THEREOF

The present invention relates to new compounds, namely capsaicin derivates, a new method for producing them and their use as micro-organism-repellent agents in paints and coatings, especially for marine installations and ships, but also for land-based installations and materials.

Ships travel faster through the water and burn less fuel when the hull is clean and smooth and free from the growth of living marine organisms.

Today tribultin (TBT) is used to prevent the growth of algae and sea plants, mussels, sea tulips and similar on ships. Such growth generates friction, which entails a rapid increase in the fuel costs. TBT is therefore added to marine paints in order to produce so-called "antifouling" paints. TBT poisons the marine organisms getting into contact with the substance, and thus keeps the ship's sides free from growth.

Unfortunately TBT has a number of environmentally negative side effects. TBT does not only affect the marine organisms trying to attach to the sides of the ship, but also poisons other marine life. Further, it has been shown that TBT is accumulated in the marine food chain and leads to unfortunate developments in various organisms. It has been shown, among other things, that TBT leads to deformation of the shell structure in oysters, sex reversal in snails and immunity disturbances as well as neurotoxic and genetic changes in other marine species.

These findings have resulted in the UN International Maritime Organization's (IMO) deciding to ban all use of TBT in marine paints. The ban will become effective as soon as the treaty has been ratified by all flag states either carrying at least 25% of the world tonnage or constituting 25% of the member countries of the IMO. The treaty will become effective on 1 Jan. 2008 at the latest, regardless of whether the above-mentioned minimum requirements are met.

Accordingly, after January 2008 there will be an absolute prohibition on the use of TBT in such paints Besides, such paints must be either physically removed or painted over with a sealer paint preventing TBT from getting into contact with the water.

Therefore, there is a need for an alternative non-toxic micro-organism-repellent agent which can replace TBT in marine paints.

According to the invention a new class of compounds can replace TBT as micro-organism-repellent agent. The new class of compounds is new derivates of a naturally existing substance, capsaicin, which is an extract from chilli (*capsicum annum*) and other pepper fruits (*capsicum fructus*).

Capsaicin ((E)-8-methyl-N-vanillyl-6-nonenamide) is extracted, as mentioned, from chilli. It is known that this extract has been used as a micro-organism-repellent in marine paints. It also has a number of other useful pharmacological properties as described in, inter alia, Dray, N. S. Biochemical Pharmacology, 44, (1992), 611.

However, the capsaicin extract has the following drawbacks, which make it unsuitable as an ingredient in "antifouling paints".

Firstly, as the extract is based on a natural raw material, the possibility of producing sufficient amounts will be subject to the same natural fluctuations as the supply of raw material, which again is dependent on the sizes, qualities, prices and similar of the crops. Today this supply of raw material is very unreliable.

Secondly, the standardized capsaicin extract contains at least 3 isomers, which all have different chemical properties but which are difficult to differentiate between. It may therefore be difficult to obtain capsaicin extracts which have sufficiently uniform purity and composition for the intended use.

Thirdly, modern marine paints are based on a chemical bonding of a repellent to a polymer base in order to prevent the repellent from being washed into the sea water immediately. The repellent, bonded to the polymer base, is liberated in step with the sea water's reacting with the polymer base. The less hydrophilic the repellent is, the longer life the marine paint will have. Natural capsaicin extracts consist of several isomers of different chemical properties and the water solubility of these isomers varies with the pH-value of the water. This will give an unwanted and non-controllable variation in the solubility properties of repellent products based on natural capsaicin extracts.

From U.S. Pat. No. 5,143,545 is known an antifouling paint containing an antibiotically active agent like chloramphenicol, for example. The risk of building up antibiotic resistance through the spreading of such antibiotics that are used to combat infectious diseases in humans, suggests that such active ingredients in an antifouling paint should be avoided.

From U.S. Pat. No. 5,226,380 is known an antifouling paint containing particles of cayenne pepper or an oleoresin *capsicum* derivate as the active agent. These active agents which are based on capsaicin or cayenne pepper are subject to the same limitations in the supply of raw materials as those discussed above. This also applies to the antifouling paint known from U.S. Pat. No. 5,397,385. It contains as an active ingredient finely powdered capsaicin, a liquid solution of an oleoresin capsaicin or a crystallized capsaicin. U.S. Pat. No. 5,629,045 also describes an antifouling paint containing, inter alia, capsaicin and vanillylamide derivates with alkyl substituents, as the active ingredient. The production of the vanillylamide derivates is based on extracts of capsaicin. The paint of U.S. Pat. No. 5,698,191 also contains a capsaicin oleo-resin in combination with a saponin compound.

It is an object of the present invention to provide an alternative to TBT, which is not poisonous and does not accumulate in the marine food chain.

It is another object of the present invention to provide an alternative to previously known capsaicin products, avoiding the problem of an unreliable supply of raw materials and fluctuations in price and quality.

It is another object of the present invention to provide an alternative to known capsaicin products, which can be produced with a defined composition and high product purity.

It is yet another object of the present invention to provide an alternative to known capsaicin products, which has defined and/or reduced hydrophilia.

It is a further object to provide products which have a broad-spectrum biological activity.

It is yet another object to provide repellent products which have an acceptable ecological profile.

The objects are realized through the features defined in the following description and subsequent Claims.

According to the present invention new chemical compounds are now provided, namely new capsaicin alkyne analogues which may be called phenylcapsaicin. The new chemical compounds according to the invention are characterized by the general formula (1),

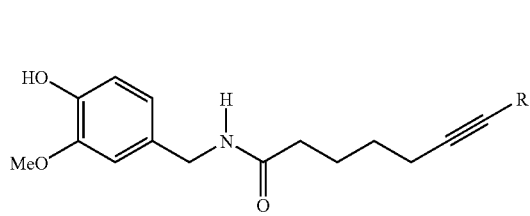

in which R is a substituent selected from the group of alkyl, alkenyl, alkynyl, allyl, aryl, alkoxy, aryloxy, alkanoyl, aroyl, amino, alkylthio, arylthio, cyano, cycloalkyl, cycloalkenyl, halo, hydroxy, oxo, nitro, trifluoromethyl;

when said substituent R contains a carbon chain, it may be straight-chained or branched and possibly further substituted with alkyl, alkenyl, alkynyl, allyl, aryl, alkoxy, aryloxy, alkanoyl, aroyl, amino, alkylthio, arylthio, cyano, cycloalkyl, cycloalkenyl, halo, hydroxy, oxo, nitro, trifluoromethyl.

When R contains a carbon chain, this carbon chain has from 1 to 8 carbon atoms, more preferably from 2 to 6 carbon atoms. Another group of preferred formula (1) compounds are those having carbon chains in R that are 1-4 carbon atoms long.

There is a particularly preferred group of compounds, in which R is an alkyl with 1-4 carbon atoms, and the most preferred compounds are those, in which R is isopropyl or propyl.

The formula (1) compounds can generally be produced by converting a carboxylic acid derivate (3) or a carboxylic acid, that is Z is HO, with a vanillylamine (2) for producing a capsaicin derivate with the formula (1), as appears from the following reaction diagram A:

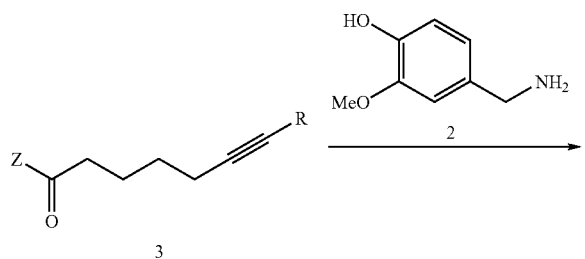

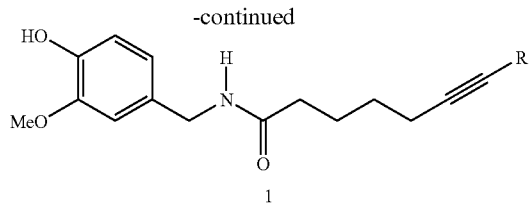

$Z=Cl, OH, R^1O, NR^1_2$ $R^1=alkyl$

R is a substituent selected from the group of alkyl, alkenyl, alkynyl, allyl, aryl, alkoxy, aryloxy, alkanoyl, aroyl, amino, alkylthio, arylthio, cyano, cycloalkyl, cycloalkenyl, halo, hydroxy, oxo, nitro, trifluoromethyl; when said substituent R contains a carbon chain, it may be straight-chained or branched, and possibly further substituted with alkyl, alkenyl, alkynyl, allyl, aryl, alkoxy, aryloxy, alkanoyl, aroyl, amino, alkylthio, arylthio, cyano, cycloalkyl, cycloalkenyl, halo, hydroxy, oxo, nitro, trifluoromethyl The carboxylic acid derivate (3) is meant to include any suitable reactant for the reaction shown in reaction diagram A and may most preferably be an ester, an amide or an acid chloride. In this description the term "carboxylic acid derivate (3)" is also meant to include the carboxylic acid (4) itself.

The vanillylamine compound (2) from vanillin can be produced as described in Kaga, H., Miura, M. and Kazuhiko, O., J. Org. Chem. 54 (1989) 3477. A yield of 42% was achieved.

The other reactant, compound (3) or (4), can be produced through the following steps:

converting an acetylene compound (8) with a protected 5-chloro-1-pentanol (7) for the production of a protected acetylene alcohol compound (6);

decomposing the protective group from the compound (6) to produce the free acetylene alcohol compound (5);

oxidizing the compound (5) for the production of the carboxylic acid (4);

and possibly transferring the acid (4) to the carboxylic acid chloride (3).

This reaction sequence is illustrated in the reaction diagram B below:

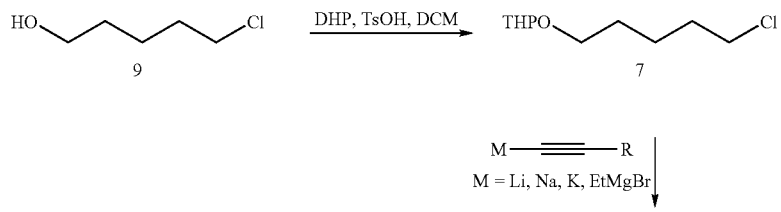

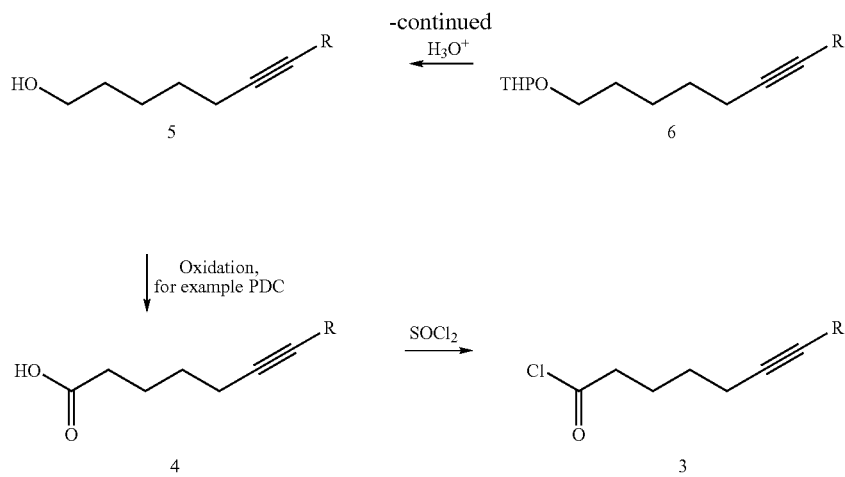

R is a substituent selected from the group of alkyl, alkenyl, alkynyl, allyl, aryl, alkoxy, aryloxy, alkanoyl, aroyl, amino, alkylthio, arylthio, cyano, cycloalkyl, cycloalkenyl, halo, hydroxy, oxo, nitro, trifluoromethyl;

when said substituent R contains a carbon chain, it may be straight-chained or branched, and possibly further substituted with alkyl, alkenyl, alkynyl, allyl, aryl, alkoxy, aryloxy alkanoyl, aroyl, amino, alkylthio, arylthio, cyano, cycloalkyl, cycloalkenyl, halo, hydroxy, oxo, nitro, trifluoromethyl.

The new capsaicin alkyne analogues with the formula (1) may be used, in one embodiment of the invention, as a micro-organism-repellent agent. This micro-organism-repellent agent can, either alone or as an ingredient in a micro-organism-repellent mixture, be included in paints or coatings to produce end products that prevent the growth of micro-organisms and other living organisms on the surface, to which the end product is applied.

Said agent or mixture can be added to a paint or a coating, so that the active formula (1) compound is present in a concentration of 0.1-50% by weight, in particular in a concentration of 0.2-10% by weight. It is preferred the most to add a formula (1) compound to a paint or coating in a concentration of 0.5-5% by weight, in particular 0.3-1% by weight.

One embodiment of the invention is a micro-organism repellent agent including a combination of two or more formula (1) compounds.

Another embodiment of the invention is a micro-organism-repellent agent including a combination of a formula (1) compound and another micro-organism-repellent agent.

Another embodiment of the invention is a micro-organism-repellent mixture, in which a formula (1) compound is included in a mixture with one or more inert additives, such as solvents, consistency modifiers, i.e. thinners or thickeners; and/or preservatives.

Yet another embodiment of the invention is a paint or coating, to which a micro-organism-repellent agent or mixture according to the invention has been added in order to prevent the growth of micro-organisms or other small organisms, like seashells, algae, sea tulips, sea plants and fungi. Such a paint, referred to as "antifouling" paint, is essentially intended for use on ships, especially ship hulls, or marine installations, such as aquacultural enclosures, quay structures and piers. It is also possible to use a micro-organism-repellent agent or mixture according to the invention in a coating which may be applied, for example, over a coat of paint in order to form a watertight surface or a surface with other desired properties.

Yet another embodiment of the invention is a paint or a coating corresponding to that described above for land-based installations and structures, in particular of the kinds based on wood, such as timber, wooden panels and similar.

A Biological Experiment

In order to illustrate the biological activity of capsaicin, a biological experiment was carried out as will described below. The experiment shows that capsaicin has the described biological activity and effect according to the invention. In other ship-bottom substances or paints capsaicin and/or other formula (1) compounds could achieve other activities in the concentrations used in this experiment.

Experimental Scheme

Capsaicin is mixed into a commercially available ship-bottom paint that has been declared free of biocides. The paint has the trade mark Fabio Eco™ and is produced by International Paint, Akzo-Nobel. 3 different concentrations were made with 0 g, 1 g and 5 g of capsaicin per kg of paint. Capsaicin was first dissolved in 10 ml of a thinner (International No. 3) and then mixed into the paint. A mixture of just Fabio Eco and 10 ml of thinner was used as a control. The paint mixture was allowed to rest for 1 hour before application. The paint was applied to a number of plexiglass panels (11×11×0.2 cm).

A total of 15 panels was painted.

5 panels with the control paint (0 g/kg capsaicin)

5 panels with 1 g/kg capsaicin 5 panels with 5 g/kg capsaicin

The painted panels were left to dry for 24 hours at 21° C. as prescribed by the producer. The panels were mounted onto an aluminium frame and put out 0.5-1 m below the sea surface on a test raft. The test raft was placed outside a marine biology laboratory with a water depth of 10 m. The panels were left for a period from 4 Jul. 2001 to 31 Aug. 2001. This period is the most growth-intensive period for marine organisms on a ship's hull and first of all for the sea tulip *Balanus improvisus*. The panels were then retrieved for immediate analysis.

Analysis of Growth

The following analyses of the panels were carried out:

The panels were photographed.

Coverage of the sea tulip *Balanus improvisus* was evaluated.

Coverage of the blue mussel *Mytilus edulis* was evaluated.

All growth on the panel was scraped off and the wet weight was determined.

BRIEF DESCRIPTION OF THE FIGURES

The results of the experiment, which are illustrated in the FIGS. 1-6, show that significantly lower growth is achieved by a treatment with a concentration of 5 g of capsaicin per kg of paint than by the control treatment.

As appears from this chart the coverage is significantly lower on surfaces treated with 5 g of capsaicin per kilo of paint than in the 2 other treatments (1-factor analysis of variance, $F_{2,12}=40.5$; $p<0.0001$). Reduction in growth is 74% measured as coverage of the sea tulip.

Figure 1:
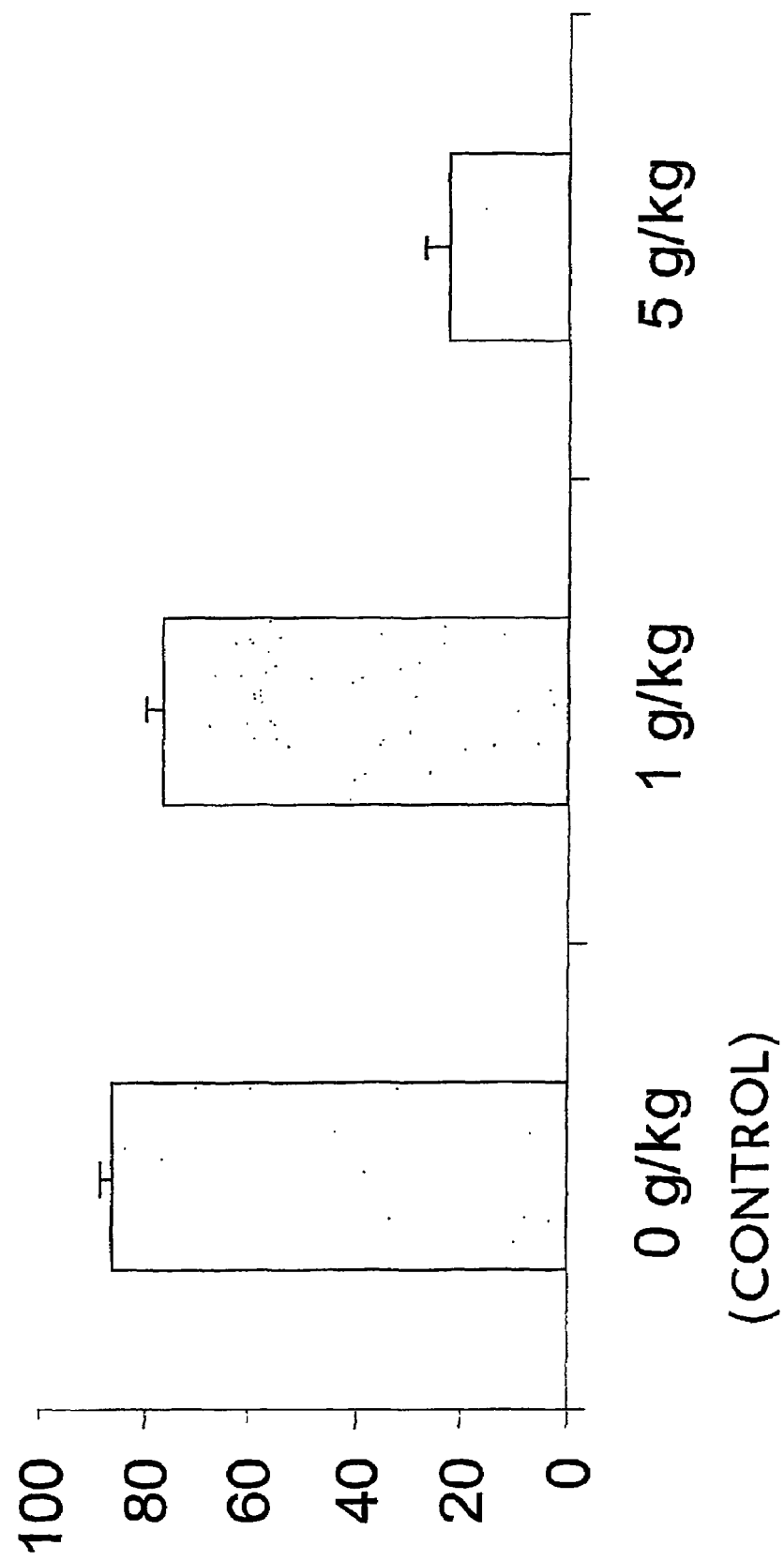
FIG. 1 shows in a bar chart the coverage of the sea tulip *Balanus improvisus* with the 3 different surface treatments. The bars denote mean values and standard deviations for 5 repetitions.
Figure 2:
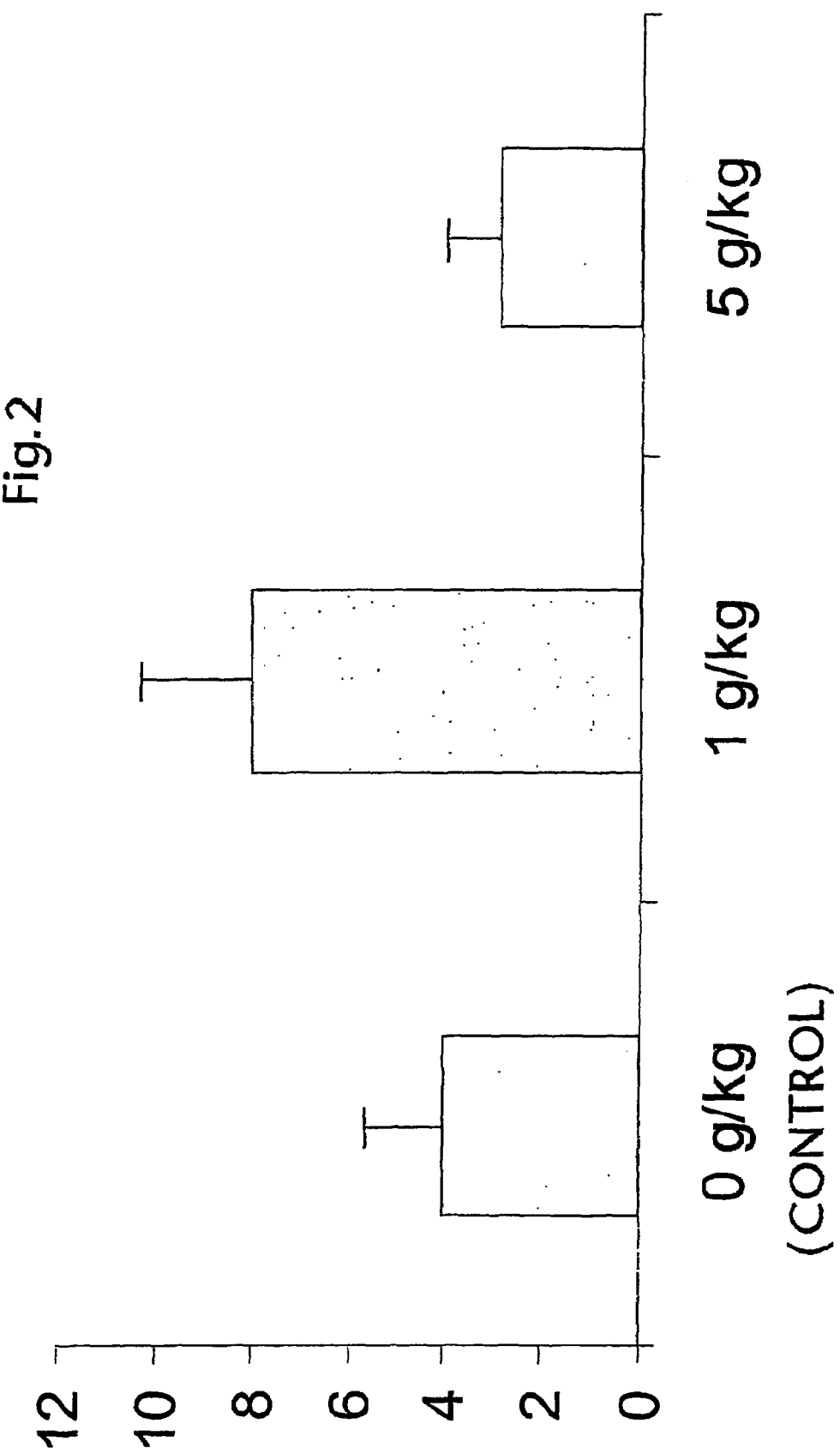

FIG. 2 shows the coverage of the blue mussel *Mytilus edulis*, in a corresponding way to that described for FIG. 1. The bars denote mean values and standard deviations for 5 repetitions.

As appears from this bar chart, there is no statistically significant difference between the 3 treatments (1-factor analysis of variance, $F_{2,12}=3.0$; $p>0.05$).

Figure 3:
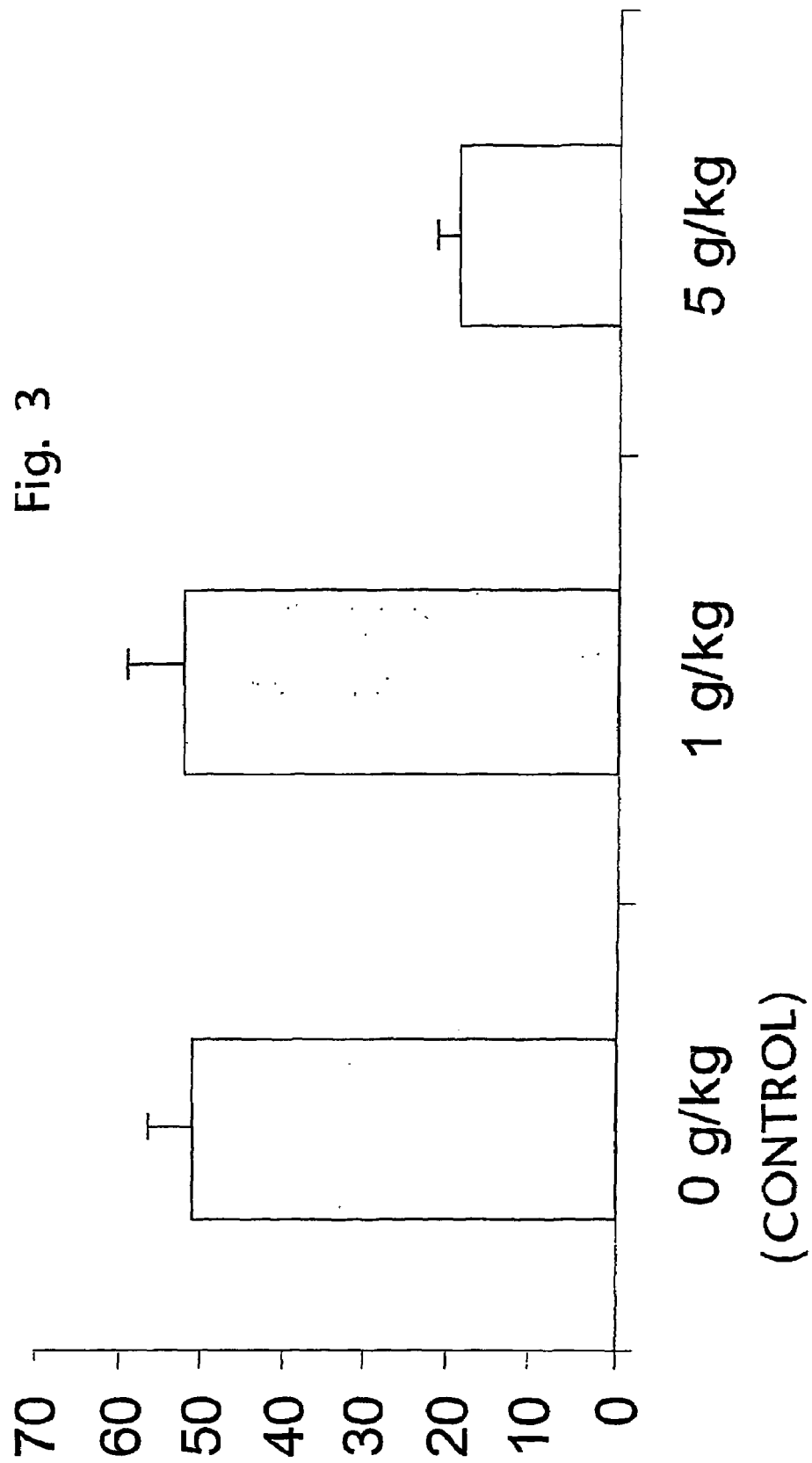

FIG. 3 shows the wet weight of the total growth on the panels for the three different treatments. The bars denote mean values and standard deviations for 5 repetitions.

As appears from this chart, the treatment with 5 g of capsaicin per kilo of paint gives a statistically lower growth than the two other treatments (1-factor analysis of variance, $F_{2,12}=12,6$; $p<0,001$). Reduction in growth is 64% measured as a reduction in wet weight of total growth.

FIG. 4 shows pictures of the five surfaces treated with the control paint (0 g/kg).

FIG. 5 shows pictures of the five surfaces treated with the lowest concentration of 1 g/kg.

FIG. 6 shows pictures of the five surfaces treated with the highest concentration of 5 g/kg. By optical comparison it can be seen clearly that the surfaces in FIG. 6 have considerably less growth than the control surfaces.

SYNTHESIS STRATEGY AND ATTEMPTS TO SYNTHESIZE PHENYLCAPSAICIN CAPSAICINOID

A detailed synthesis description for the new compounds is given below. References are made to some literature collected in a literature list at the end. Several synthesis methods for capsaicin and other capsaicinoids are known.[5-9] In the present case the biological activity of capsaicin on marine micro-organisms is of particular interest. In order to produce more potent capsaicinoids, a synthesis strategy for derivates of capsaicin has been developed, in which the carbon-carbon double bond has been replaced by a carbon-carbon triple bond. A general synthesis strategy is shown in diagram 1.

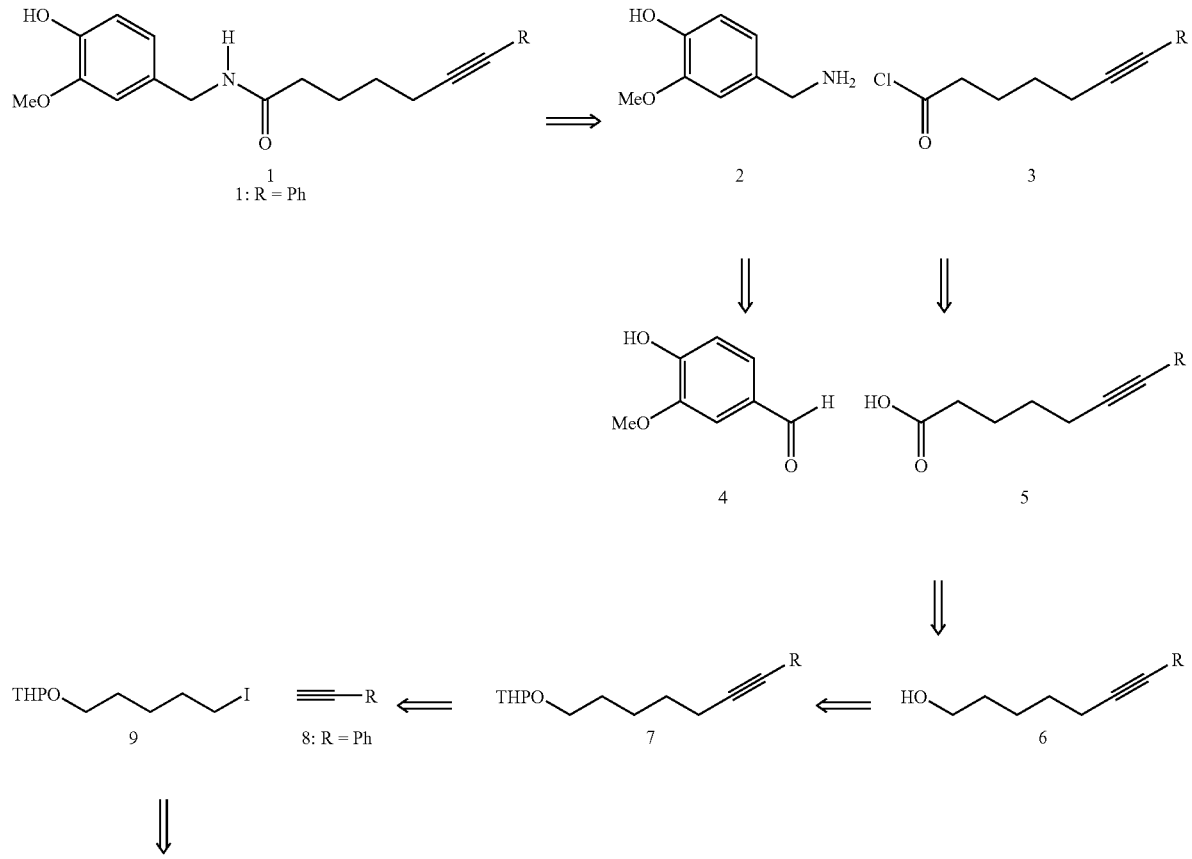

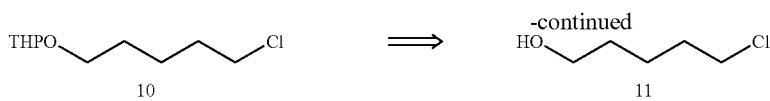

Diagram 1. Retrosynthetic Analysis of Capsaicin Alkyne Analogues.

The synthesis strategy for capsaicin alkyne analogues is general with respect to the alkyne base material 8 (R=aryl, alkyl etc.). By varying the R-group different capsaicin alkyne analogues can be synthesized, and can thereby be evaluated with a view to biological activity. The first target molecule 1 (R=Ph) yields the alkyne phenylacetylene (8: R=Ph) and 4-hydroxy-3-methoxybenzaldehyde (vanillin) (4) and 5-chloro-1-pentanol (11) as base materials. 4-aminomethyl-2-methoxyphenol (vanillylamine) (2) was synthesized from vanillin (4) as described in the literature.[6] 5-Chloro-1-pentanol (11) was first protected as a THP ether by the use of standard reaction conditions.[10,11] The corresponding THP ether (10) was formed in a 95% yield. Attempts at a substitution reaction (SN2) with lithium phenylacetylide in THF did not give a desired product (7) because lithium phenylacetylide reacted as a base and HCl elimination ($E_2$) from 10 was observed with the result that the corresponding alkene was the only product formed. Sodium phenylacetylide gave the same result. This problem was solved by 10 being converted into the corresponding iodine analogue 9 in a Finkelstein reaction.[11-13] Now the substitution reaction went excellently and the alkyne 7 was formed in an 85% yield. Acid-catalysed removal of the THP protection[10] in 7 gave the alcohol 6 in an almost quantitative yield (97%). A modified Brown's chromic acid oxidation[14] gave the carboxylic acid 5 in a 90% yield. 5 was then reacted with thionyl chloride and the corresponding acid chloride 3 was formed in an 85% yield. The coupling reaction with the acid chloride (3) and vanillylamine (2) gave the target molecule 7-phenylhept-6-yne-acid-4-hydroxy-3-methoxybenzylamide (1) in an 86% yield, which, as far as the inventors know, has never been synthesized before. The inventors suggest phenylcapsaicin as trivial name for 1.

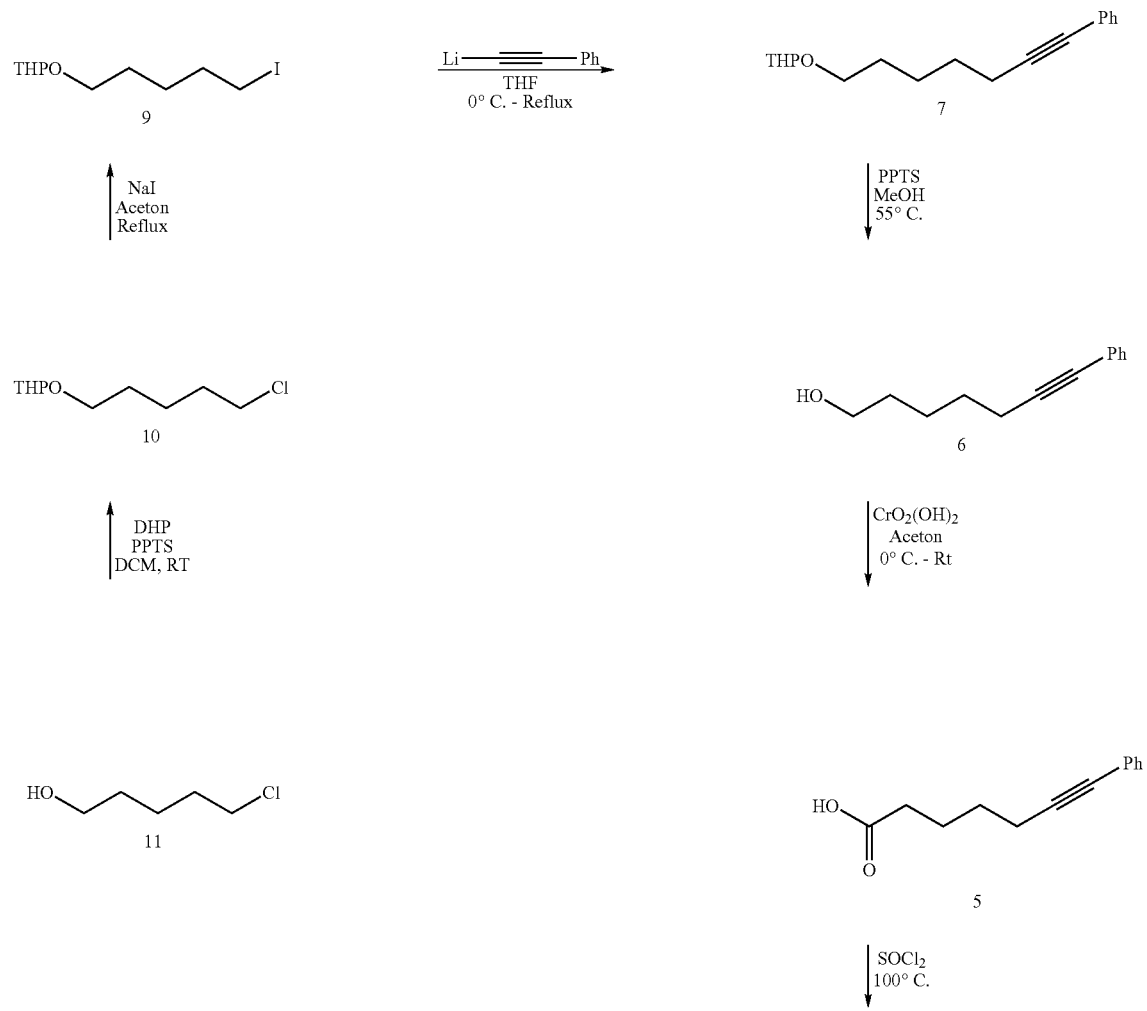

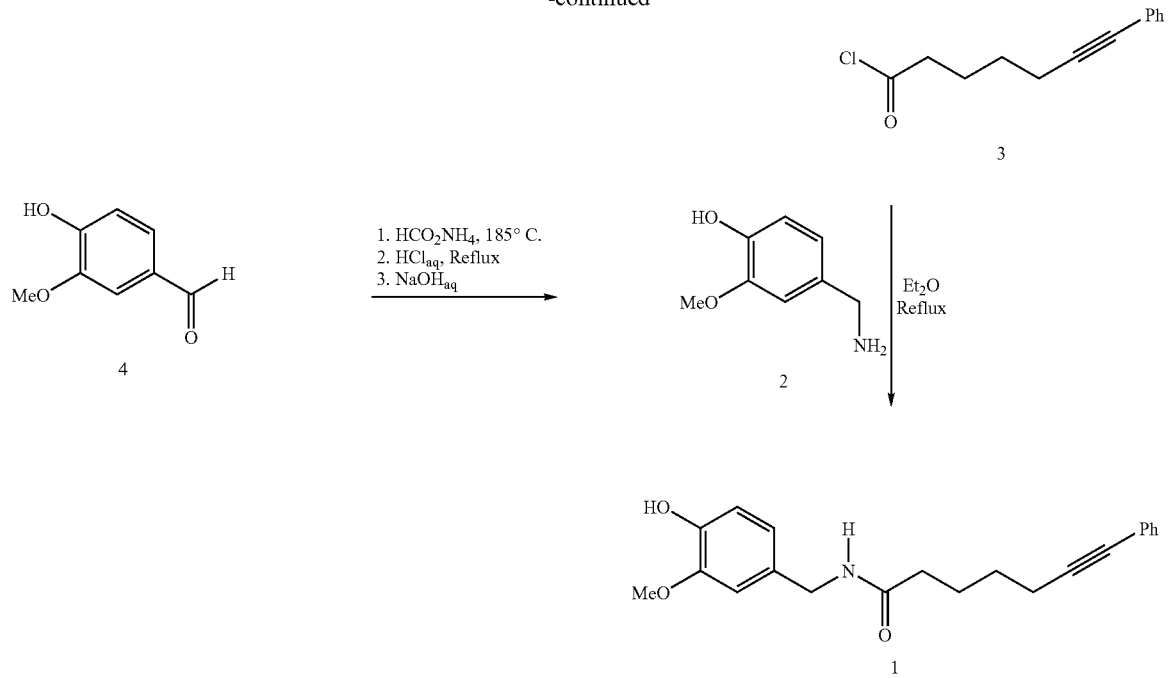

Diagram 2. Experimental

General:

Nuclear magnetic resonance spectroscopy, NRM 300 MHz $^1$H-NMR spectra and 75 MHz $^{13}$C-NMR spectra were acquired on a Varian 300 MHz spectrometer. Tetramethylsilane (TMS) was used as the internal standard. Chemical shifts for $^1$H-NMR spectra are given in ppm relative to TMS. $^{13}$C-NMR spectra are given in ppm relative to deuterated chloroform (δ 76.9 ppm). Thin-layer chromatography was performed on silica gel plates from Fluka (silica gel/DC-Alufolien silica gel with fluorescent indicator, prod. No. 60778). The spots were detected with ultraviolet light, UV (λ=254 nm) or with MOP reagent (molyb-dato-phosphoric acid (14 g) in ethanol (125 mL) or CER-MOP reagent (molybdato-phosphoric acid (5 g), cerium(IV)sulphate (2 g) and 98% $H_2SO_4$ (16 ml) in water (180 mL)) and developed by heating the silica gel plates with a hot-air pistol. Chemicals were supplied by Fluka, Sigma Aldrich, Acros, Merck and Lancaster. Standard drying methods were used when necessary. Dry tetrahydrofuran was generated from sodium-benzophenon-ketyl under argon.

2-(5-chloropentyloxy)tetrahydro-2H-pyrane (10)

5-chloro-1-pentanol (12.26 g, 0.1 mol) was dissolved in dry dichloromethane (400 mL). 3,4-Dihydro-2H-pyrane (12.62 g, 0.15 mol) and pyridine toluene-4-sulphonate (1.26 g, 5 mmol) was then added and the reaction mixture was stirred magnetically in a nitrogen atmosphere at room temperature over night. Sodium-hydrogen-carbonate, saturated solution (150 mL) was added and the phases were separated. The aqueous phase was then extracted with dichloromethane (4×25 mL). The combined dichloromethane phases were washed with water (2×20 mL) and then dried (MgSO$_4$). Dichloromethane was then distilled out on a rotary evaporator and yielded 19.6 g (95%) of a pale yellow oil. NMR indicated a pure product.

2-(5-iodpentyloxy)tetrahydro-2H-pyrane (9)

A solution of 2-(5-chloropentyloxy)tetrahydro-2H-pyrane (10) (20.67 g, 0.1 mol) in dry acetone (50 mL) was added in drops to a magnetically stirred solution of sodium iodide (16.49 g, 0.11 mol) in dry acetone (150 mL). The reaction mixture was refluxed in a nitrogen atmosphere over night. After cooling the precipitated sodium chloride was filtered out and acetone was distilled out on a rotary evaporator. The residue which still contained some sodium chloride was dissolved in dry pentane (200 mL). Sodium chloride was filtered out and pentane distilled out on a rotary evaporator, yielding 26.2 g (88%) of a yellowish brown oil. NMR indicated a pure product.

2-(7-phenylhept-6-ynyloxy)tetrahydro-2H-pyrane (7)

BuLi (33.3 mL, 50 mmol, 1.5 M) was added in drops to a magnetically stirred solution of phenyl acetylene (5.11 g, 50 mmol) in dry tetrahydrofuran (200 mL) at 0° C. in a nitrogen atmosphere. After all the BuLi had been added, the reaction mixture was stirred at 0° C. for 30 minutes. A solution of 2-(5-iodpentyloxy)tetrahydro-2H-pyrane (9) (14.91 g, 50 mmol) in dry tetrahydrofuran (100 mL) was added in drops at 0° C. Adding completed, the reaction mixture was allowed to reach room temperature in order then to be refluxed over night. The reaction was monitored by thin-layer chromatography (TLC). When all the base material had been converted, water (300 mL) was added and the aqueous phase was extracted with petroleum ether (boiling point 40-60° C.) (6×50 mL). The combined organic phases were washed with water (4×25 mL) and dried (MgSO$_4$). Petroleum ether was distilled out on a rotary evaporator, yielding 11.6 g (85%). NMR indicated a pure product, and further purification was therefore not necessary.

7-phenylhept-6-yn-1-ol (6)

Pyridine toluene-4-sulphonate (0.75 g, 3 mmol) was added to a magnetically stirred solution of 2-(7-phenylhept-6-ynyloxy)-tetrahydro-2H-pyrane (7) (13.62 g, 50 mmol) in dry methanol (300 mL). The reaction mixture was stirred at 55° C. and monitored by TLC. When all the base material had been converted, methanol was distilled out on a rotary evaporator and water (200 mL) was added to the residue. The aqueous phase was extracted with petroleum ether (boiling point 40-60° C.)/Et$_2$O 1:1 (5×50 mL). The combined organic phases were washed with water (2×20 mL) and dried (MgSO$_4$). Distillation on a rotary evaporator yielded 9.1 g (97%) of a yellow viscous oil. TLC and NMR indicated a pure product.

7-phenylhept-6-yne acid (5)

Brown's chromic acid reagent (133 mL, 88 mmol, 0.66 M) was added slowly in drops to a magnetically stirred solution of 7-phenylhept-6-yn-1-ol (6) (7.53 g, 40 mmol) in acetone (400 mL) at 0° C. After the chromic acid had been added, the reaction mixture was stirred for 1 hour at 0° C. and then at room temperature until all the base material has been converted as indicated by TLC. Water (300 mL) was added and the aqueous phase was then extracted with petroleum ether (boiling point 40-60° C.)/Et$_2$O 1:1 (6×50 mL). The combined organic phases were washed with water (2×25 mL) and dried (MgSO$_4$). Distillation on a rotary evaporator yielded 7.3 g (90%) of a pale yellow viscous oil, which crystallized when left to rest. TLC and NMR indicated a pure product.

7-phenylhept-6-ynoyl chloride (3)

A magnetically stirred mixture of 7-phenylhept-6-yne acid (5) (4.05 g, 20 mmol) and thionyl chloride (7.14 g, 60 mmol) was refluxed (100° C.) for 2 hours. Excess thionyl chloride was removed on a rotary evaporator, yielding 3.7 g (85%) of a brown oil. TLC and NMR indicated a pure product.

Vanillylamine (2):

Vanillylamine was synthesized on a 100 mmol scale as described in the literature.[6]

7-phenylhept-6-yne-acid-4-hydroxy-3-methoxybenzylamide (phenylcapsaicin) (1)

A solution of 7-phenylhept-6-ynoyl chloride (3) (10 mmol, 2.21 g) in dry Et$_2$O (25 mL) was added in drops to a suspension of vanillylamine (2) (3.06 g, 20 mmol) in dry Et$_2$O (75 mL) in an argon atmosphere. The reaction mixture was refluxed until TLC indicated that the base materials had been converted. Diethyl ether was removed on a rotary evaporator, yielding 2.9 g (86%) of a yellow viscous oil which crystallized when left to rest. TLC and NMR indicated a pure product.

REFERENCES

[1] A. Dray, *Biochem. Pharmacol.* 1992, 44, 611.
[2] M. J. Caterina, M. A. Schumacher, M. Tominaga, T. A. Rosen, J. D. Levine. D. Julius, *Nature* 1997, 389, 816.
[3] P. Holzer, *Pharmacol. Rev.* 1991, 43, 143.
[4] T. R. LaHahn, R. W. Farmer, *Proc. West. Pharmacol Soc.* 1983, 26, 145
[5] P. M. Gannett, D. L. Nagel, P. J. Reilly, T. Lawson, J. Sharpe, B. Toth, *J. Org. Chem.* 1988, 53, 1064.
[6] Kaga, H., Miura, M. and Kazuhiko, O. *J. Org. Chem.* 1989, 54, 3477.
[7] K. Kobata, K. Yoshikawa, M. Kohashi, T. Watanabe, *Tetrahedron Lett.* 1996, 37, 2789.
[8] H. Kaga, K. Goto, T. Takahashi, M. Hino, T. Tokuhashi, K. Orito, *Tetrahedron* 1996, 52, 8451.
[9] O. Dasse, A. Mahadevan, L. Han, B. R. Martin, V. Di Marzo, R. K. Razdan, *Tetrahedron* 2000, 56 9195.
[10] M. Miyashita, A. Yoshikoshi, P. A. Grieco, *J. Org. Chem.* 1977, 42, 3772.
[11] K. J. Shea, L. D. Burke, *J. Org. Chem.* 1988, 53, 318.
[11] H. Finkelstein, *Chem. Ber.* 1910, 43, 1528
[12] G. D. Branum, *Tetrahedron Lett.* 1981, 22, 2055.
[13] M. F. Sartori, *Chem. Rev.* 1951, 48, 237.
[14] H. C. Brown, C. P. Garg, K. T. Liu, *J. Org. Chem.* 1971, 63, 387

The invention claimed is:

1. A chemical compound, characterized in that it has the general formula

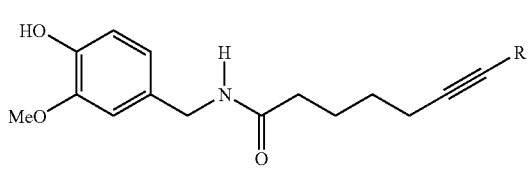

in which R is a substituent selected from the group of C$_1$-C$_{18}$ alkyl, trifluoromethyl, C$_3$-C$_{12}$ cycloalkyl, phenyl, phenoxy, phenylthio, halogen.

2. A method for the production of a chemical compound of the formula,

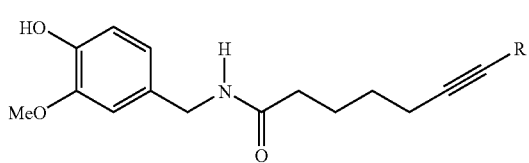

characterized by reaction of a carboxylic acid or a carboxylic acid derivate

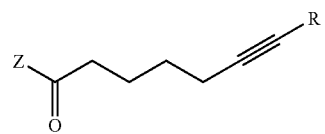

in which Z is one of Cl, OH, R$^1$O, NR$^1{}_2$ and R$^1$ is alkyl and R is a substituent selected from the group of C$_1$-C$_{18}$ alkyl, trifluoromethyl, C$_3$-C$_{12}$ cycloalkyl, phenyl, phenoxy, phenylthio, halogen, with a vanillylamine

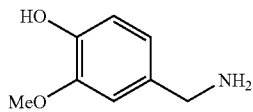

wherein a capsaicin derivate of formula 1 is produced.

3. A method according to claim 2, characterized by the further proceeding steps of:

converting an acetylene compound

in which M is Li, Na, K, EtMgBr with a protected 5-chloro-1-pentanol

for producing a protected acetylene alcohol compound

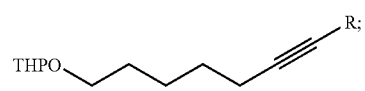

decomposing the protective group from this compound in order to produce the free acetylene alcohol compound

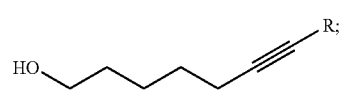

oxidizing this compound in order to produce the acetylene carboxylic acid

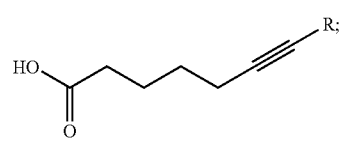

transferring the carboxylic acid to a carboxylic acid derivate

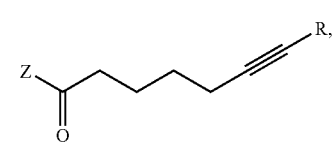

in which Z is Cl, $R^1O$, $NR^1{}_2$, and $R^1$.

4. A method of repelling a microorganism using a chemical compound, comprising:

providing the chemical compound with the formula according to

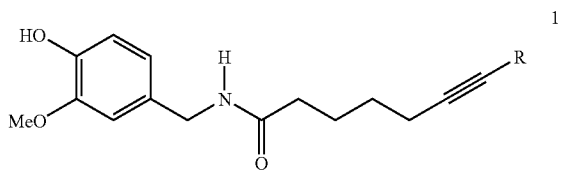

in which R is a substituent selected from the group of $C_1$-$C_{18}$ alkyl, trifluoromethyl, $C_3$-$C_{12}$ cycloalkyl, phenyl, phenoxy, phenylthio, halogen; and repelling the microorganism utilizing the compound.

5. A method according to claim 2, characterized by the further proceeding steps of:

converting an acetylene compound

in which M is Li, Na, K, EtMgBr with a protected 5-chloro-1-pentanol

for producing a protected acetylene alcohol compound

decomposing the protective group from this compound in order to produce the free acetylene alcohol compound

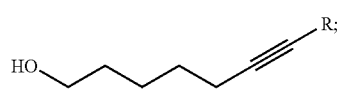

oxidizing this compound in order to produce the acetylene carboxylic acid

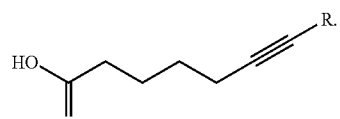

6. A method according to claim 2, characterized by the further proceeding steps of:

converting an acetylene compound

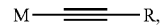

in which M is Li, Na, K, EtMgBr with a protected 5-chloro-1-pentanol

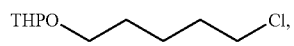

for producing a protected acetylene alcohol compound

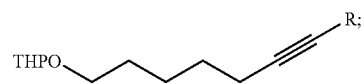

decomposing the protective group from this compound in order to produce the free acetylene alcohol compound

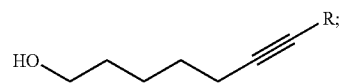

oxidizing this compound in order to produce the acetylene carboxylic acid

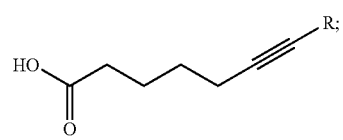

transferring the carboxylic acid to a carboxylic acid derivate that is an acid chloride

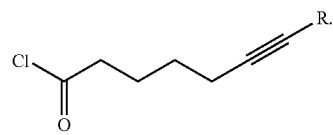

7. The method of claim 4, wherein the compound is to paint.

8. The method of claim 4, wherein the compound is added to a coating composition.

9. The method of claim 4, wherein the compound is applied to a ship.

10. The method of claim 4, wherein the compound is applied to wood.

11. The method of claim 4, wherein a mixture includes the compound and the mixture is applied to a surface.

* * * * *

UNITED STATES PATENT AND TRADEMARK OFFICE
CERTIFICATE OF CORRECTION

PATENT NO. : 7,446,226 B2 Page 1 of 1
APPLICATION NO. : 10/571658
DATED : November 4, 2008
INVENTOR(S) : Helsing et al.

It is certified that error appears in the above-identified patent and that said Letters Patent is hereby corrected as shown below:

In the Claims Section:

Column 18, Claim 7, Line 19, please insert --added-- after is.

Signed and Sealed this

Twenty-third Day of June, 2009

JOHN DOLL
*Acting Director of the United States Patent and Trademark Office*